US012745970B2

(12) United States Patent
Nolewaika et al.

(10) Patent No.: US 12,745,970 B2
(45) Date of Patent: Sep. 29, 2026

(54) RELIABLE FIRST-FAULT-SAFETY DETECTION OF COLLISIONS IN MEDICAL DEVICES

(71) Applicant: Siemens Healthineers AG, Forchheim (DE)

(72) Inventors: Martin Nolewaika, Erlangen (DE); Harald Karl, Fuerth (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 59 days.

(21) Appl. No.: 18/947,080

(22) Filed: Nov. 14, 2024

(65) Prior Publication Data

US 2025/0160766 A1 May 22, 2025

(30) Foreign Application Priority Data

Nov. 17, 2023 (DE) ..................... 10 2023 211 466.6

(51) Int. Cl.
*A61B 6/10* (2006.01)
*A61B 6/00* (2006.01)
*G05B 19/04* (2006.01)

(52) U.S. Cl.
CPC ................ *A61B 6/102* (2013.01); *A61B 6/54* (2013.01); *G05B 19/04* (2013.01); *A61B 6/4441* (2013.01)

(58) Field of Classification Search
CPC ......... A61B 6/102; A61B 6/4441; A61B 6/54; G05B 19/04
See application file for complete search history.

(56) References Cited

U.S. PATENT DOCUMENTS

| | | | | |
|---|---|---|---|---|
| 2015/0128727 A1* | 5/2015 | Sattler | A61B 6/102 73/862.625 |
| 2016/0297074 A1* | 10/2016 | Divoky | B25J 9/1674 |
| 2017/0052670 A1* | 2/2017 | Gemmel | G16H 40/63 |

(Continued)

FOREIGN PATENT DOCUMENTS

| | | | | |
|---|---|---|---|---|
| DE | 202022103669 U1 | 1/2023 | |
| DE | 102022204210 A1 | 11/2023 | |
| WO | WO-2019201506 A1 * | 10/2019 | A61G 7/018 |

OTHER PUBLICATIONS

WO 2019/201506 A1 with translation (Year: 2019).*

(Continued)

*Primary Examiner* — Mark R Gaworecki
(74) *Attorney, Agent, or Firm* — Harness, Dickey & Pierce, P.L.C.

(57) ABSTRACT

In the normal mode of a medical device, a control apparatus moves a moving element of the medical device in a controlled manner via a drive when corresponding movement commands are issued. In the normal mode, an evaluation apparatus monitors a first-fault-safety contact element arranged on the medical device for actuation and, in the event of actuation, transmits a normal collision signal via lines to the control apparatus and a monitoring apparatus. In the event of a normal collision signal being transmitted to it, the control apparatus immediately ends the movement of the moving element, at least in the current direction of travel, and, at the latest after a predetermined waiting time has elapsed without actuation of the drive as such, the monitoring apparatus prevents the drive from acting on the moving element.

10 Claims, 6 Drawing Sheets

(56) References Cited

U.S. PATENT DOCUMENTS

| | | | |
|---|---|---|---|
| 2020/0073786 | A1 | 3/2020 | Schat et al. |
| 2021/0055718 | A1 | 2/2021 | Rathgeb et al. |
| 2022/0297706 | A1 | 9/2022 | Nilsson et al. |
| 2024/0074720 | A1 | 3/2024 | Mueller et al. |

OTHER PUBLICATIONS

IEC 60601 Edition 3.2 2020-08; IEC Standard 60601-1: Edition 3.2, Consolidated version. Aug. 2020.

Hesse, C. et al., "Collision avoidance of medical devices with (radar) sensors," 2022.

* cited by examiner

RELIABLE FIRST-FAULT-SAFETY DETECTION OF COLLISIONS IN MEDICAL DEVICES

CROSS-REFERENCE TO RELATED APPLICATION(S)

The present application claims priority under 35 U.S.C. § 119 to German Patent Application No. 10 2023 211 466.6, filed Nov. 17, 2023, the entire contents of which are incorporated herein by reference.

FIELD

One or more example embodiments is based on an operating method for a medical device, wherein, in a normal mode of the medical device, a control apparatus moves a moving element of the medical device in a controlled manner via a drive when corresponding movement commands are issued to the control apparatus of the medical device.

SUMMARY

The drive is usually position-controlled. However, this is not absolutely necessary. In individual cases, speed control or torque control can also be used. In the normal mode, the control apparatus receives signals characteristic of the movement of the moving element from a sensor element (for example from a position encoder or speed encoder of the drive) during the controlled movement of the moving element and takes them into account in the actuation of the drive.

One or more example embodiments is further based on a medical device having a moving element, a drive and a control apparatus, wherein, in a normal mode of the medical device, the control apparatus moves the moving element in a controlled manner via the drive when corresponding movement commands are issued to the control apparatus.

BRIEF DESCRIPTION OF THE DRAWINGS

Properties, features and advantages and the manner in which they are achieved will become clearer and more plainly comprehensible in conjunction with the following description of the exemplary embodiments explained in more detail in conjunction with the drawings. These show in schematic representation.

DETAILED DESCRIPTION

Figure 1:
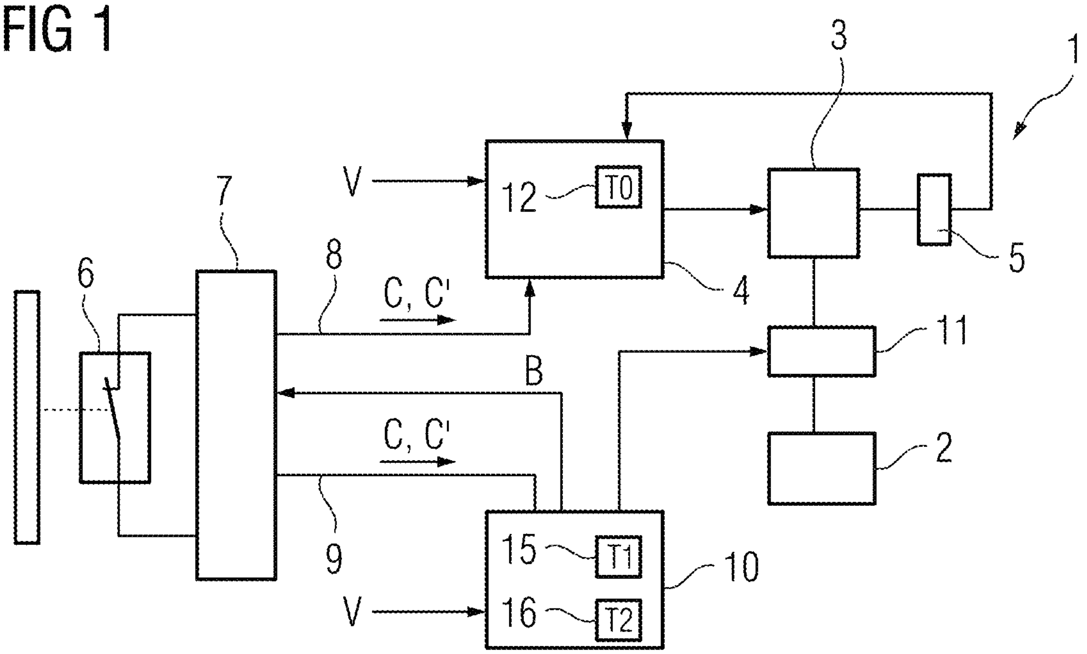
FIG. 1 illustrates a medical device according to one or more example embodiments.

An example of such devices are C-arm systems that can be moved around a patient table. In this case, the moving element can, for example, be the C-arm or an element of the C-arm. It can also be a medical imaging system. In this case, the moving element can, for example be a patient couch of the medical imaging system. Another example is medical devices that are moved as a whole on the floor, wherein wheels of the medical device are driven in such a way that the movement is effected or at least supported via an electric drive. In this case, the moving element can, for example, be a driven wheel. Other medical devices are also conceivable.

The medical sector is increasingly using medical devices that have moving elements powered via an electric drive. The increasing electrification of movement also increases the risk of causing damage, in particular personal injury. Due to the increasingly complex degrees of freedom of movement, it is not always possible, or not possible to a sufficient extent, for staff to monitor the movement. Therefore, reliable collision detection is required to minimize the risk of damage.

In the prior art, various sensors are used to detect a collision. Examples of such sensors are so-called bumpers, movable covers equipped with micro keys, and force sensors. In the prior art, the signals from these sensors are detected and evaluated via fail-safe industrial control systems. These should then initiate a stop to the movement in the event of a collision.

The use of fail-safe industrial control systems is not common in the medical sector. In the medical sector, it is more common to implement first-fault safety for moving axes of a medical device according to IEC 60601 using a C-path and a parallel P-path. Here, "C" stands for control and "P" stands for protection or monitoring. Therefore, in contrast to a safe industrial control system in which all signals are processed in parallel on at least two channels including parallel first-fault-safety actuation, there is only a single path available for actuating the drive (namely the C-path). In this case, first-fault safety is ensured by the parallel P-path, but this does not actuate the drive and can only execute a safety-related action in the event of a fault; this typically entails triggering a brake or switching off the electrical power supply to the drive.

One or more example embodiments creates possibilities via which first-fault-safety collision detection can be implemented in a simple manner even in the case of a C-path and a parallel P-path as commonly implemented in the medical sector.

According to one or more example embodiments, an operating method of the type mentioned in the introduction is embodied in that,

- in the normal mode of the medical device,
- an evaluation apparatus of the medical device monitors a first-fault-safety contact element arranged on the medical device, in particular on the moving element, for actuation and, in the event of actuation, transmits a respective normal collision signal via respective lines to the control apparatus and a monitoring apparatus of the medical device which is different from the control apparatus,
- in the event of a normal collision signal being transmitted to it, the control apparatus immediately ends the movement of the moving element, at least in the current direction of travel, and
- in the event of a normal collision signal being transmitted to it, at the latest after a predetermined waiting time has elapsed without actuation of the drive as such, the monitoring apparatus prevents the drive from acting on the moving element,
- either the control apparatus or the monitoring apparatus transmits a check command to the evaluation apparatus on the occurrence of a checking condition,
- in the event of a check command being transmitted to it, the evaluation apparatus transmits a respective special collision signal to the control apparatus and the monitoring apparatus via the lines and in the absence of a special collision signal expected on the basis of a check command, the control apparatus immediately blocks movement of the moving element, at least in the current direction of travel, and, at the latest after the predetermined waiting time has elapsed without actuation of the drive as such, the monitoring apparatus prevents the drive from acting on the moving element.

The monitoring apparatus is a pure monitoring apparatus (according to IEC 60601). Therefore, there is no parallel safety-related actuation of the drive by the control apparatus and the monitoring apparatus. Therefore, the monitoring apparatus does not have to receive any signals characteristic of the movement of the moving element. It merely prevents the drive from acting on the moving element in the event of a normal collision signal being transmitted to it or in the absence of an expected special collision signal. The waiting time is determined by the conditions of the medical device. It is usually (slightly) longer than the time required by the drive to stop the moving element. The type of action taken by the monitoring apparatus can vary. For example, the monitoring apparatus can actuate a brake that is arranged in the drive train from the drive to the moving element. Alternatively, the monitoring apparatus can actuate a clutch so that the power transmission from the drive to the moving element is interrupted. It is likewise possible for the monitoring apparatus to switch off the electrical power supply to the drive.

Depending on the individual case, the control apparatus can, in addition to ending the movement of the moving element (i.e., setting the corresponding actuation of the drive), additionally actuate a (possibly further) brake. However, this is not necessary in all cases. This is in particular not necessary if the kinematic chain from the drive to the moving element has a self-blocking effect in the absence of actuation.

In the event of a normal collision signal or in the absence of an expected special collision signal, the monitoring apparatus and the control apparatus can further additionally output a corresponding message, for example to a higher-level apparatus. As an alternative to or in addition to transmission to a higher-level apparatus, the message can also be output to an operator of the medical device, for example via a visual signal (for example, a flashing alarm light), via an acoustic signal (for example a beep) or via a haptically detectable signal (for example, the extension of a pin).

The check command is output by either the control apparatus or the monitoring apparatus. The apparatus that outputs the check command is automatically aware that a special collision signal is expected. The other apparatus in each case can be aware of the corresponding facts due to other circumstances. It is, for example, conceivable that the apparatus that outputs the check command informs the other apparatus in each case that it has output the check command. However, preferably, the other apparatus can deduce from other facts that a special collision signal is expected. This will be discussed in more detail below.

In one possible embodiment of the operating method, the evaluation apparatus is embodied as a first-fault-safety evaluation apparatus. In this case, the checking condition can consist in the fact that the medical device is in a special mode in which actuation of the drive is blocked by the control apparatus.

The fact that the medical device is in a special mode can also be known automatically to the other apparatus in each case, i.e., the apparatus that does not transmit the check command to the evaluation apparatus.

For example, in the event that the control apparatus generates the check command, a timer can be started within the monitoring apparatus due to the occurrence of the special mode (i.e., at the start of the special mode), wherein the timer runs for a certain time period, for example 30 seconds. During this time period, the control apparatus does not actuate the drive. If a collision signal is transmitted to the monitoring apparatus via the lines during this time period, the monitoring apparatus can automatically interpret this collision signal as a special collision signal.

Conversely, if the monitoring apparatus generates the check command, a timer can be started within the control apparatus due to the occurrence of the special mode, wherein the timer runs for a certain time period, for example 30 seconds. During this time period, the control apparatus does not actuate the drive. If a collision signal is transmitted to the control apparatus via the lines during this time period, the control apparatus can automatically interpret this collision signal as a special collision signal.

If the checking condition consists in the medical device being in a special mode, it must be ensured that the time period between immediately successive checks is shorter than the MFOT (multiple fault occurrence time). This can always be guaranteed in practice. However, this requires the evaluation apparatus to be embodied as a first-fault-safety evaluation apparatus so that a single fault does not lead to an unsafe state.

The special mode can, for example, consist in a power supply of the medical device having been switched on shortly beforehand, or in a command for transition to a special mode having been issued by a higher-level apparatus.

When the power supply is switched on, the medical device (or its entire electronics) is in a ramp-up phase. In the ramp-up phase, no drives are actuated. Thus, immediately after the power supply is switched on, the special mode is established automatically. The higher-level apparatus can request the transition to a special mode, for example, in each case after a predetermined time has elapsed (for example, every 8 hours).

In addition, it is possible for a normal collision signal to have a minimum duration and for a special collision signal to have a duration that is considerably shorter than the minimum duration.

This procedure represents a further possibility for distinguishing between a normal collision signal and a special collision signal. For example, it can be known from the actual conditions of the specific medical device that, in the event of an actual collision, a collision signal has a duration of at least 500 ms. In this case, the special collision signal can be made to have a very short duration of, for example, 1 ms (or less), either by an appropriate design of the evaluation apparatus or by an appropriate embodiment (in particular duration) of the check command. Such a short duration cannot occur at all for the specific medical device in the case of a normal collision signal. This enables a safe and reliable distinction to be made between a normal collision signal and a special collision signal. The numerical values given are examples only. They can vary according to the type of medical device and the type of possible collision.

As an alternative to checking during a special mode, it is possible for the checking condition to consist in the expiration of a predetermined monitoring period, for a normal collision signal to have a minimum duration and for a special collision signal to have a duration that is considerably shorter than the minimum duration.

In this case, the control apparatus or the monitoring apparatus repeatedly transmits a check command to the evaluation apparatus after the predetermined monitoring period has elapsed in each case.

Of course, this procedure can also be implemented if the evaluation apparatus is embodied as a first-fault-safety evaluation apparatus. In contrast to a check only in a special mode of the medical device, however, this procedure can also provide sufficient fault safety if the evaluation apparatus is not embodied as a first-fault-safety evaluation apparatus. It is only necessary to select a sufficiently short monitoring period, for example to set it to a value of 100 ms. In general, the criterion is that the monitoring period must be shorter than the so-called FTT (fault tolerance time). In this case, the distinction between a normal collision signal and a special collision signal can be made on the part of the other control apparatus and monitoring apparatus based on the duration of the collision signal. On the one hand, the duration of the special collision signal must be considerably shorter than the monitoring period and, on the other, also considerably shorter than the minimum duration of a normal collision signal.

According to one or more example embodiments, a medical device of the type mentioned in the introduction is embodied such

- that the medical device has an evaluation apparatus, a monitoring apparatus different from the control apparatus and a first-fault-safety contact element arranged on the medical device, in particular on the moving element,
- that, for transmitting collision signals, the evaluation apparatus is connected to the control apparatus and the monitoring apparatus via respective lines and
- that the control apparatus, the evaluation apparatus and the monitoring apparatus interact with one another in accordance with an operating method according to one or more example embodiments.

In one possible embodiment, the evaluation apparatus is embodied as a first-fault-safety evaluation apparatus. In this case, the control apparatus, the evaluation apparatus and the monitoring apparatus can interact according to a correspondingly embodied operating method in which the evaluation apparatus must be embodied as a first-fault-safety evaluation apparatus. Here, once again, the advantages achieved thereby correspond to those of the corresponding operating method.

Furthermore, as before, it is possible for the control apparatus, the evaluation apparatus and the monitoring apparatus to interact with one another according to an operating method in which the checking condition consists in the expiration of a predetermined monitoring period, a normal collision signal has a minimum duration and a special collision signal has a duration that is considerably shorter than the minimum duration. Here, once again, the advantages achieved correspond to those of the corresponding operating method.

According to FIG. 1, a medical device 1 has a moving element 2. The moving element 2 can, for example, be a wheel, with which the medical device 1 is moved as a whole on a floor. Alternatively, the moving element 2 can be a part of the medical device 1 that is moved relative to another part of the medical device 1. The moving element 2 is moved via an (electric) drive 3 of the medical device 1.

The medical device 1 furthermore has a control apparatus 4. In a normal mode of the medical device 1, movement commands V can be issued to the control apparatus 4 from outside, for example by a higher-level control apparatus (not depicted) or by an operator (likewise not depicted). In the normal mode, in response to the issue of movement commands V, the control apparatus 4 moves the moving element 2 in a controlled manner via the drive 3. Therefore, a sensor system 5 is assigned to the drive 3 (alternatively to the moving element 2) via which sensor signals characteristic of the moving element 2 can be detected and fed to the control apparatus 4. The control apparatus 4 takes the sensor signals into account when ascertaining the actuation of the drive 3. Position control is usually used, but in some cases speed control or alternatively torque control is also used.

The medical device 1 furthermore has a first-fault-safety contact element 6. Possible embodiments of the contact element 6 are known to those skilled in the art. The contact element 6 is arranged on the medical device 1. In some cases, the contact element 6 can be arranged on the moving element 2. In other cases, as depicted in FIG. 1, the contact element 6 is arranged on another element of the medical device 1, for example a cover sheet.

The medical device 1 also has an evaluation apparatus 7. The evaluation apparatus 7 is connected to the control apparatus 4 via a line 8 and to a monitoring apparatus 10 via a further line 9. The evaluation apparatus 7 monitors the contact element 6 for actuation. In the event of actuation, the evaluation apparatus 7 transmits a collision signal C to the control apparatus 4 via the line 8 and a collision signal C to the monitoring apparatus 10 via the further line 9. The collision signals C will be referred to as normal collision signals C in the following. The reason for this designation will become clear later.

Figure 2:
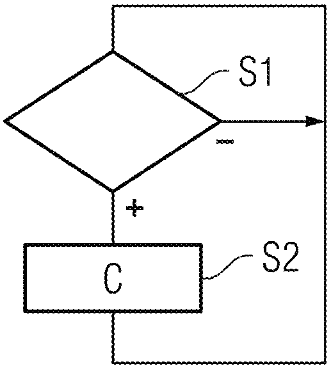
FIGS. 2 to 7 illustrate flow charts according to one or more example embodiments.
Figure 3:
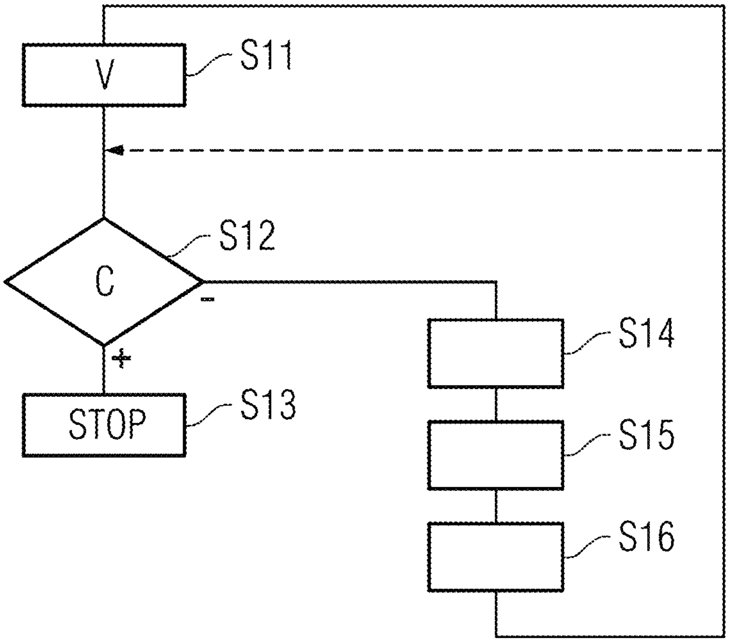
Figure 4:
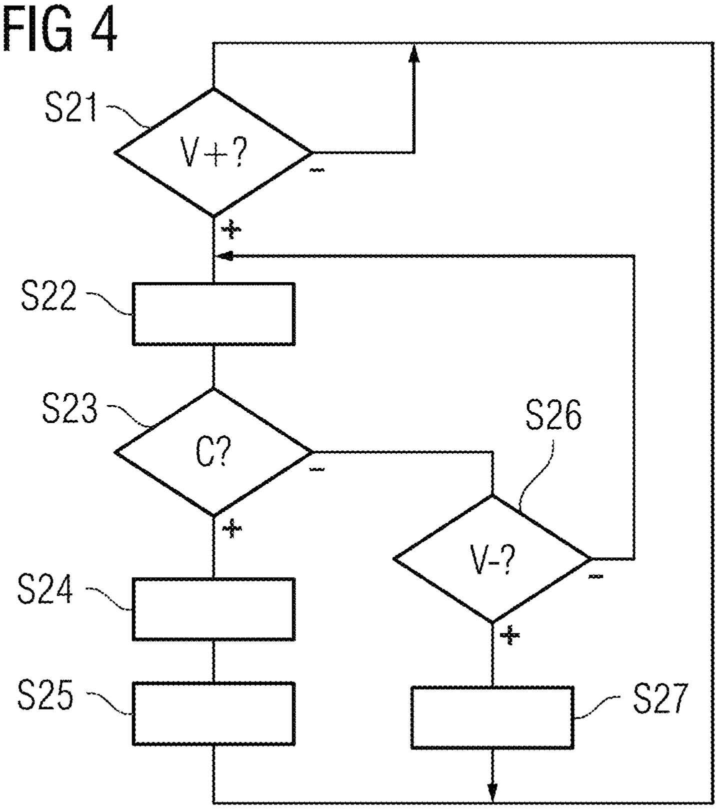

The following describes the basic operating principles of the evaluation apparatus 7, the control apparatus 4 and the monitoring apparatus 10 in conjunction with FIGS. 2 to 4. These procedures will be modified later in order to explain the present invention in more detail.

According to FIG. 2, the evaluation apparatus 7 checks in step S1 whether the contact element 6 has been actuated. If this is the case, the evaluation apparatus 7 transmits the (normal) collision signals C to the control apparatus 4 and the monitoring apparatus 10 via the lines 8, 9 in step S2. The evaluation apparatus 7 performs steps S1 and S2 iteratively repeatedly.

The present explanation of the operating principle of the evaluation apparatus 7 corresponds in the way it is presented to the execution of a program by a microprocessor or the like. However, this is not usually the case. As a rule, the evaluation apparatus 7 is implemented purely in terms of circuitry.

According to FIG. 3, the control apparatus 4 receives the movement commands V in step S11. In step S12, the control apparatus 4 checks whether a (normal) collision signal C has been transmitted to it by the evaluation apparatus 7. If this is the case, the control apparatus 4 proceeds to step S13. In step S13, the control apparatus 4 immediately ends the active actuation of the drive 3 and thus the movement of the moving element 2, at least in the current direction of travel. Further movement of the moving element may be permitted in the opposite direction of travel. If the control apparatus 4 does not receive a (normal) collision signal C, the control apparatus 4 proceeds to step S14. In step S14, the control apparatus 4 receives the sensor signals from the sensor system 5. In step S15, the control apparatus 4 ascertains actuation commands for the drive 3. When ascertaining the actuation commands, the control apparatus 4 takes into account both the movement commands V and the sensor signals. In step S16, the control apparatus 4 outputs the ascertained actuation commands to the drive 3. The control apparatus 4 then returns to step S11 or, as shown by the dashed line in FIG. 3, to step S12. Whether the control apparatus 4 returns to step S11 or step S12 can depend on the type of movement commands V. Thus, the control apparatus 4 executes steps S11 to S16 iteratively repeatedly. However, the iterative execution is aborted in the event of a collision.

The monitoring apparatus 10 of the medical device 1 is a different device from the control apparatus 4. According to FIG. 4, the monitoring apparatus 10 initially checks in step S21 whether the movement command V is also issued to it. If the movement command V is not issued, the monitoring apparatus 10 returns to step S21. If the movement command V is issued, the monitoring apparatus 10 releases the movement of the moving element 2 in step S22. For example, the monitoring apparatus 10 can release a brake 11 (FIG. 1) of the medical device 1 in step S22.

In step S23, the monitoring apparatus 10 checks whether a (normal) collision signal C has been transmitted to it by the evaluation apparatus 7. If this is the case, the monitoring apparatus 10 proceeds to step S24. In step S24, the monitoring apparatus 10 prevents the drive from acting on the moving element 2 at the latest after a predetermined waiting time has elapsed without actuation of the drive 3 as such, thereby blocking further movement of the moving element 2. In step S25, the monitoring apparatus 10 then waits for a release signal. Only after the release signal has been issued does the monitoring apparatus 10 return to step S21.

On the other hand, if no (normal) collision signal C was transmitted to the monitoring apparatus 10 by the evaluation apparatus 7, the monitoring apparatus 10 proceeds from step S23 to step S26. In step S26, the monitoring apparatus 10 checks whether the movement command V is no longer issued. If this is the case, the monitoring apparatus 10 proceeds to step S27. In step S27, the monitoring apparatus 10 prevents the drive 3 from acting on the moving element 2, at the latest after the predetermined waiting time has elapsed without actuation of the drive 3 as such. The monitoring apparatus 10 then returns to step S21. On the other hand, if the movement command V continues to be issued, the monitoring apparatus 10 returns from step S26 to step S22 (alternatively to step S23).

A check command B (see FIG. 1) can be transmitted to the evaluation apparatus 7. Transmission can be carried out by the control apparatus 4. Alternatively, but not additionally, transmission can be carried out by the monitoring apparatus 10. Depending upon which of the two apparatuses 4, 10 transmits the check command B, the corresponding apparatus 4, 10 is therefore connected to the evaluation apparatus 7 for this purpose. In the following, it is always assumed that transmission is carried out by the monitoring apparatus 10. However, the reverse procedure is completely equivalent and analogous.

The check command B is transmitted to the evaluation apparatus 7 on the occurrence of a checking condition. The following explains various possibilities for the checking condition in conjunction with the other FIGS. However, as depicted in FIG. 1, regardless of the type of checking condition, the evaluation apparatus 7 always transmits a collision signal C' to the control apparatus 4 and the monitoring apparatus 10 via the lines 8, 9 when a check command B is transmitted to it. In the following, the collision signals C' are referred to as special collision signals C'.

In situations in which they expect a special collision signal C' based on a check command B, the control apparatus 4 and the monitoring apparatus 10 check whether a special collision signal C' is actually transmitted to them by the evaluation apparatus 7. If the special collision signal C' is transmitted to them, the normal mode of the medical device 1 is started or continued. On the other hand, if the special collision signal C' is not received, the control apparatus 4 immediately blocks a movement of the moving element 2, at least in the current direction of travel. Therefore, the control apparatus 4 does not start moving the moving element 2 at all or ends the movement of the moving element 2. Likewise, the monitoring apparatus 10 prevents the drive 3 from acting on the moving element 2 at the latest after the predetermined waiting time has elapsed without actuation of the drive 3.

Figure 5:
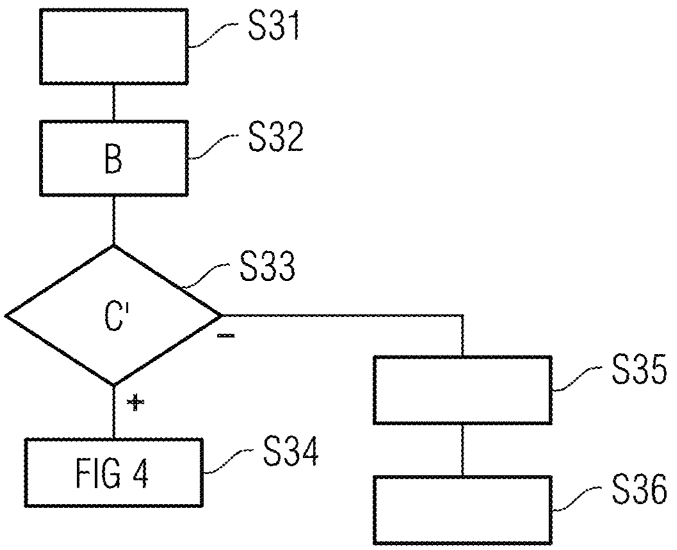
Figure 6:
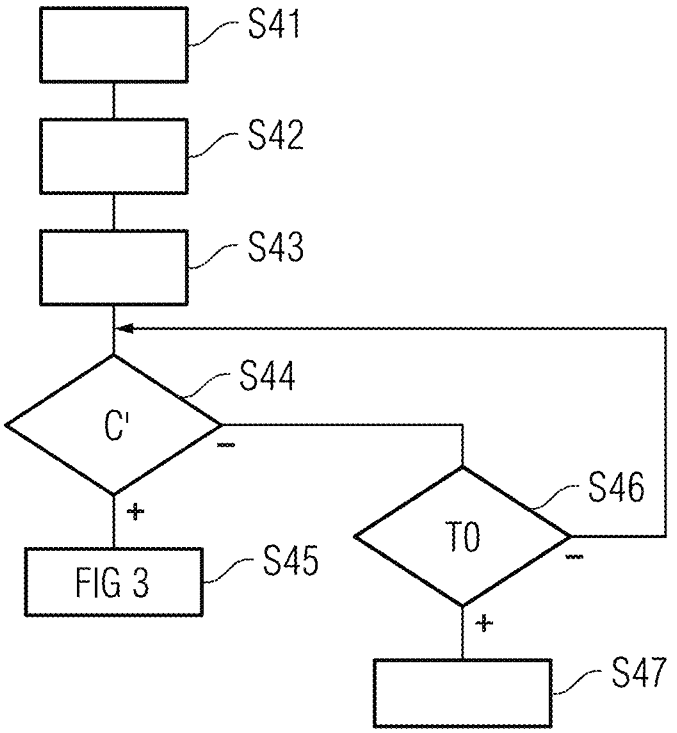
Figure 7:
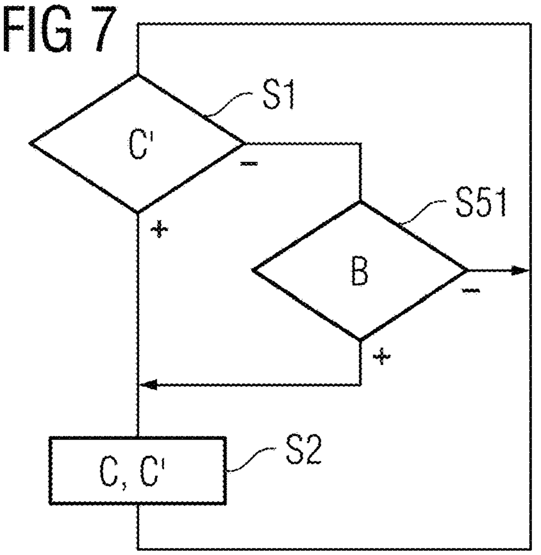

The following explains a possible procedure for implementing this procedure in conjunction with FIGS. 5 to 7.

As far as FIGS. 5 and 6 are concerned, it is relevant that, as an alternative to the normal mode, the medical device 1 can be in a special mode. The special mode can, for example, consist in a power supply of the medical device 1 having been switched on shortly beforehand. In this case, the medical device 1 is in ramp-up mode. It is also possible that a higher-level apparatus (not depicted) has issued a command for transition to a special mode. In the event of a dedicated special mode, the control apparatus 4 and the monitoring apparatus 10 are also in a special mode.

In the special mode, the monitoring apparatus 10 can, for example, implement a procedure such as that explained below in conjunction with FIG. 5. According to FIG. 5, the monitoring apparatus 10 initially switches to the special mode in step S31. In step S32, the monitoring apparatus 10 transmits the check command B to the evaluation apparatus 7. In step S33, the monitoring apparatus 10 checks whether a collision signal C' is transmitted to it by the evaluation apparatus 7. Due to the fact that the monitoring apparatus 10 is in the special mode, the monitoring apparatus 10 knows that a collision signal C, C' transmitted by the evaluation apparatus 7 is a special collision signal C'. If the evaluation apparatus 7 transmits the special collision signal C', the monitoring apparatus 10 switches to the normal mode (FIG. 4), indicated by step S34. If the evaluation apparatus 7 does not transmit the special collision signal C', the monitoring apparatus 10 proceeds to step S35. In step S35, the monitoring apparatus 10 prevents the drive 3 from acting on the moving element 2 without actuation of the drive 3 as such. If necessary, the monitoring apparatus 10 can additionally output an error message to a higher-level apparatus or to an operator in step S36. A step analogous to step S36 can also take place following step S24 in FIG. 4.

In a similar way, in the special mode, the control apparatus 4 can, for example, implement a procedure such as that explained below in conjunction with FIG. 6. According to FIG. 6, the control apparatus 4 initially switches to the special mode in step S41. In a subsequent step S42, the control apparatus 4 blocks actuation of the drive 3.

In step S43, the control apparatus 4 starts a timer 12 (see FIG. 1). The timer 12 runs for a predetermined time period T0, for example 30 seconds. In step S44, the control apparatus 4 checks whether a collision signal C' is transmitted to it by the evaluation apparatus 7. Due to the fact that the control apparatus 4 is in the special mode, the control apparatus 4 knows that a collision signal C, C' transmitted by the evaluation apparatus 7 is a special collision signal C'. If the evaluation apparatus 7 transmits the special collision signal C', the control apparatus 4 switches to the normal mode (FIG. 3), indicated by step S45.

If the evaluation apparatus 7 does not transmit the special collision signal C', the control apparatus 4 proceeds to step S46. In step S46, the control apparatus 4 checks whether the timer 12 has expired. If this is not the case, the control apparatus 4 returns to step S44. On the other hand, if the timer 12 has expired, the procedure in FIG. 6 is ended from the outset. In particular, the control apparatus 4 does not switch to the normal mode. As a result, the control apparatus 4 retains the blocking of the drive 3 (in this case regardless of the direction of travel). If necessary, the control apparatus 4 can additionally output an error message to the higher-level apparatus or to the operator in step S47. A step analogous to step S47 can also take place following step S13 in FIG. 3.

The evaluation apparatus 7 likewise executes a slightly modified method compared to FIG. 2. This method is explained below in conjunction with FIG. 7. According to FIG. 7, the procedure in FIG. 2 is supplemented by step S51. In step S51, the evaluation apparatus 7 checks whether a check command B is issued to it. If this is the case, the evaluation apparatus 7 transmits a collision signal, in this case a special collision signal C', to the control apparatus 4 and the monitoring apparatus 10, even if it has not detected a collision in step S1. Reference is made once again to the fact that, despite the representation in the form of a flow chart, the evaluation apparatus 7 is generally implemented purely in terms of circuitry.

Figure 8:
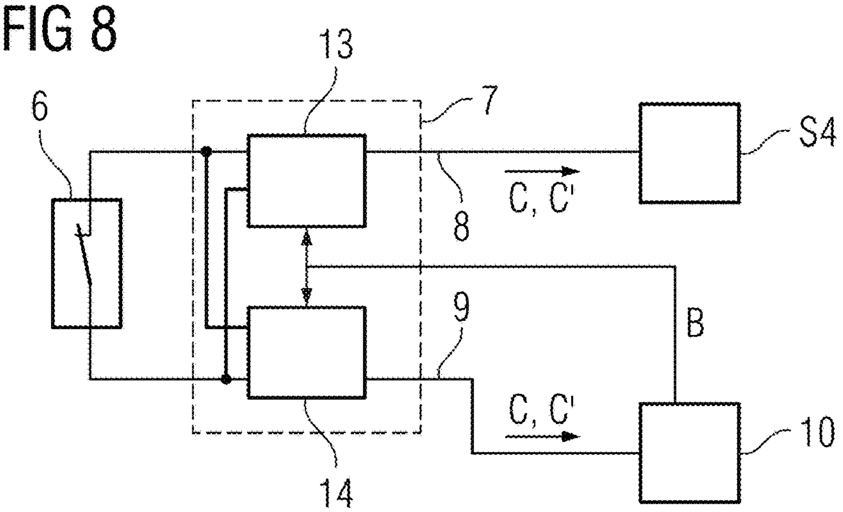
FIG. 8 illustrates an evaluation apparatus according to one or more example embodiments.

In the case of the procedure according to FIGS. 5 to 7, in particular FIGS. 5 and 6, the evaluation apparatus 7 according to FIG. 8 is embodied as a first-fault-safety evaluation apparatus. Therefore, the evaluation apparatus 7 comprises two independent blocks 13, 14, wherein both blocks 13, 14 monitor the contact element 6 for actuation independently of one another and, in the event of actuation, transmit a (normal) collision signal C. The block 13 transmits a normal collision signal C to the control apparatus 4, the block 14 transmits a normal collision signal C to the monitoring apparatus 10. The check command B is also fed to both blocks 13, 14, independently of one another, so that the two blocks 13, 14 may also transmit a special collision signal C' to the control apparatus 4 or the monitoring apparatus 10 independently of one another.

Possibilities for a first-fault-safety embodiment of the evaluation apparatus 7 are generally known to those skilled in the art and so no further explanations are necessary in this regard.

Figure 9:
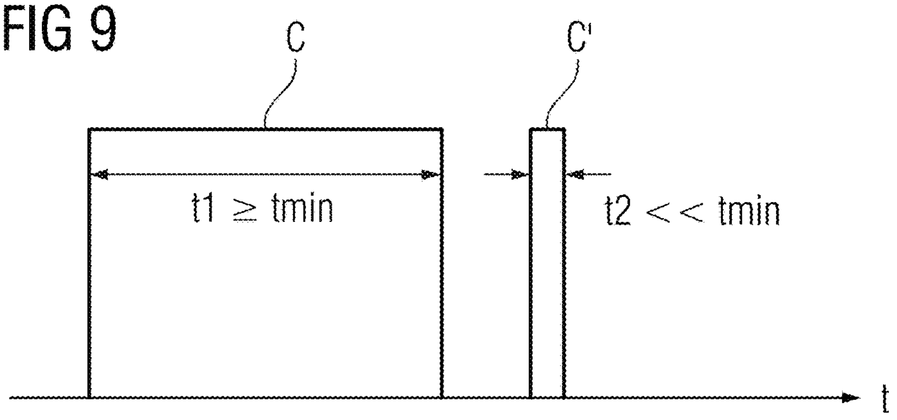
FIG. 9 illustrates a timing diagram according to one or more example embodiments.

Other ways of distinguishing between a normal collision signal and a special collision signal C, C' are also possible. In particular, the duration of a collision signal C, C' can be used to distinguish whether it is a normal collision signal C or a special collision signal C'. For example, according to FIG. 9, due to the intrinsic properties of the medical device 1, it can be known that a collision, if one occurs, always has a duration t1 that is at least as long as a minimum duration tmin. The minimum duration tmin can, for example, be 100 ms or 500 ms. Of course, other values are also possible. If it can be ensured that a special collision signal C' has a duration t2 that is significantly shorter than the minimum duration tmin, the duration of the collision signal C, C' can be used to distinguish whether this is a normal collision signal C or a special collision signal C'. In this case, the distinction is possible regardless of whether the control apparatus 4 and/or the monitoring apparatus 10 is in the normal mode or in the special mode. The duration t2 can, for example, be a maximum of 10% of the minimum duration tmin. Of course, even smaller values are also possible. With a minimum duration tmin of, for example, 100 ms, the duration t2 can, for example, be 5 ms, 2 ms, 1 ms and even smaller values. The duration t2 can, for example, be set by the embodiment of the evaluation apparatus 7, i.e., its reaction to the transmission of a check command B. Likewise, it is also possible that, due to the embodiment of the evaluation apparatus 7, the duration of the special collision signal C' corresponds to the duration of the check command B and that the check command B has the duration t2.

As just mentioned, if the duration t2 is suitably determined, a distinction between a normal collision signal C and a special collision signal C' is also possible when the control apparatus 4 and the monitoring apparatus 10 are in the normal mode. Alternatively to the procedure in FIGS. 5 and 6, it is therefore possible to operate the control apparatus 4 and the monitoring apparatus 10 according to methods as explained below in conjunction with FIGS. 10 and 11.

Figure 10:
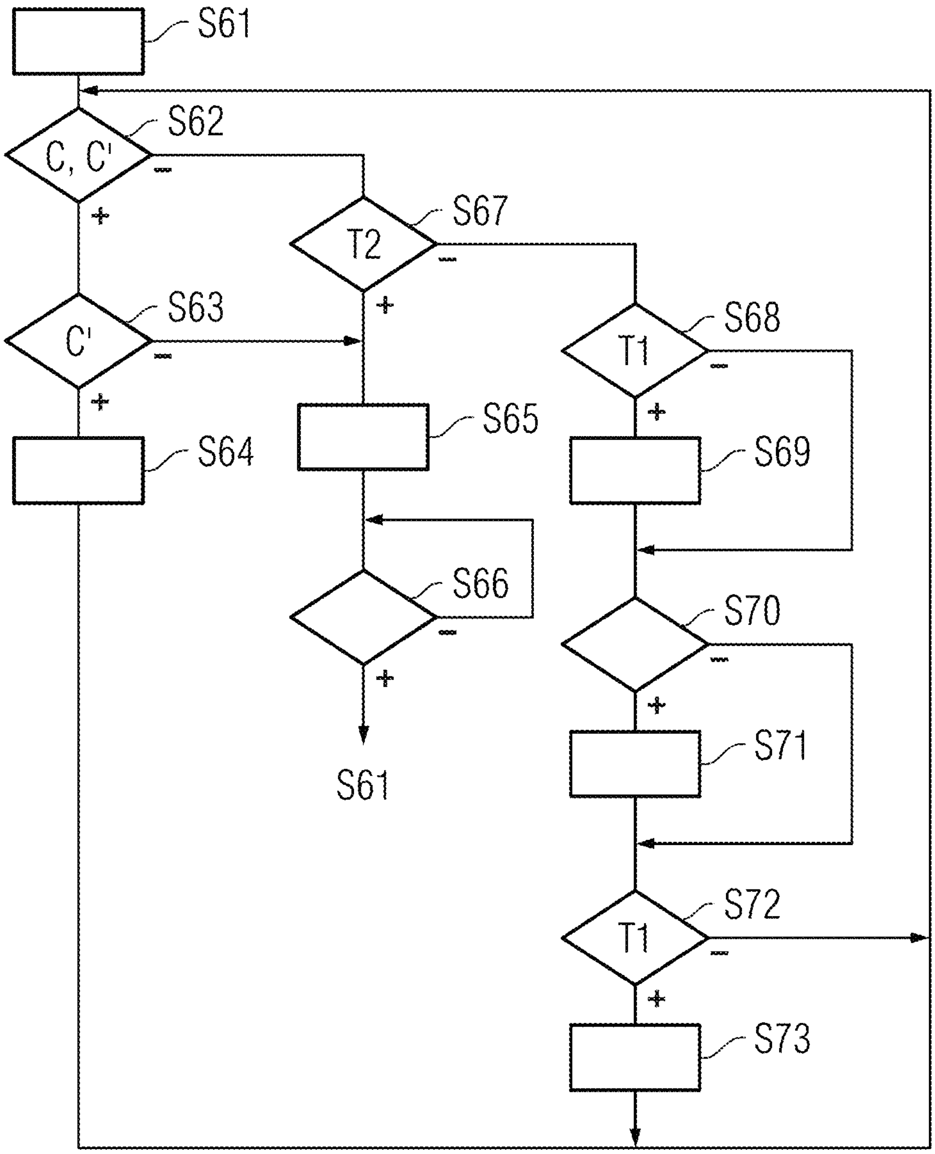
FIGS. 10 and 11 illustrate flow charts according to one or more example embodiments.

According to FIG. 10, in step S61, the monitoring apparatus 10 starts two timers 15, 16 (see FIG. 1). The timer 15 runs for a time period T1, the timer 16 for a time period T2. The time period T2 is (often only slightly) longer than the time period T1. In step S62, the monitoring apparatus 10 checks whether a collision signal C, C' has been transmitted to it by the evaluation apparatus 7. If this is the case, the monitoring apparatus 10 proceeds to step S63. In step S63, the monitoring apparatus 10 checks whether the transmitted collision signal C, C' has (exactly or at least approximately) the duration t2. If this is the case, the transmitted collision signal C, C' is a special collision signal C'. Therefore, the monitoring apparatus 10 proceeds to step S64 in which it resets the two timers 15, 16 so that the time periods T1, T2 start to run again. From step S64, the monitoring apparatus 10 returns to step S62. Otherwise, the transmitted collision signal C, C' is a normal collision signal C. Therefore, the monitoring apparatus 10 proceeds to step S65. In step S65, the monitoring apparatus 10 prevents the drive 3 from acting on the moving element 2 at the latest after the predetermined waiting time has elapsed without actuation of the drive 3 as such, thereby blocking further movement of the moving element 2. In step S66, the monitoring apparatus 10 then blocks a release signal. Only after the release signal has been issued does the monitoring apparatus 10 return to step S61. Steps S65 and S66 correspond to steps S24 and S25 in FIG. 4.

If the monitoring apparatus 10 does not detect a collision signal C, C' in step S62, the monitoring apparatus 10 proceeds to step S67. In step S67, the monitoring apparatus 10 checks whether the timer 16 has expired. If this is the case, there is a malfunction of the evaluation apparatus 7 because a special collision signal C' was requested but not transmitted. Therefore, the monitoring apparatus 10 proceeds to step S65.

If the timer 16 has not yet expired, the monitoring apparatus 10 proceeds to step S68. In step S68, the monitoring apparatus 10 checks whether the timer 15 has expired. If this is the case, the monitoring apparatus 10 proceeds to step S69 in which it transmits a check command B to the evaluation apparatus 7 and thus requests a special collision signal C'. Otherwise, the monitoring apparatus 10 skips to step S69.

In step S70, the monitoring apparatus 10 checks whether the movement command V is also issued to it. If the movement command V is issued, the monitoring apparatus 10 releases the movement of the moving element 2 in step S71. Otherwise, the monitoring apparatus 10 skips step S71.

The monitoring apparatus 10 then checks in step S72 whether the movement command V is not issued to it. If this is the case, the monitoring apparatus 10 proceeds to step S73. In step S73, the monitoring apparatus 10 prevents the drive 3 from acting on the moving element 2, at the latest after the predetermined waiting time has elapsed without actuation of the drive 3 as such. Otherwise, the monitoring apparatus 10 skips step S73. In both cases, i.e., both with and without execution of step S73, the monitoring apparatus 10 then returns to step S62.

Figure 11:
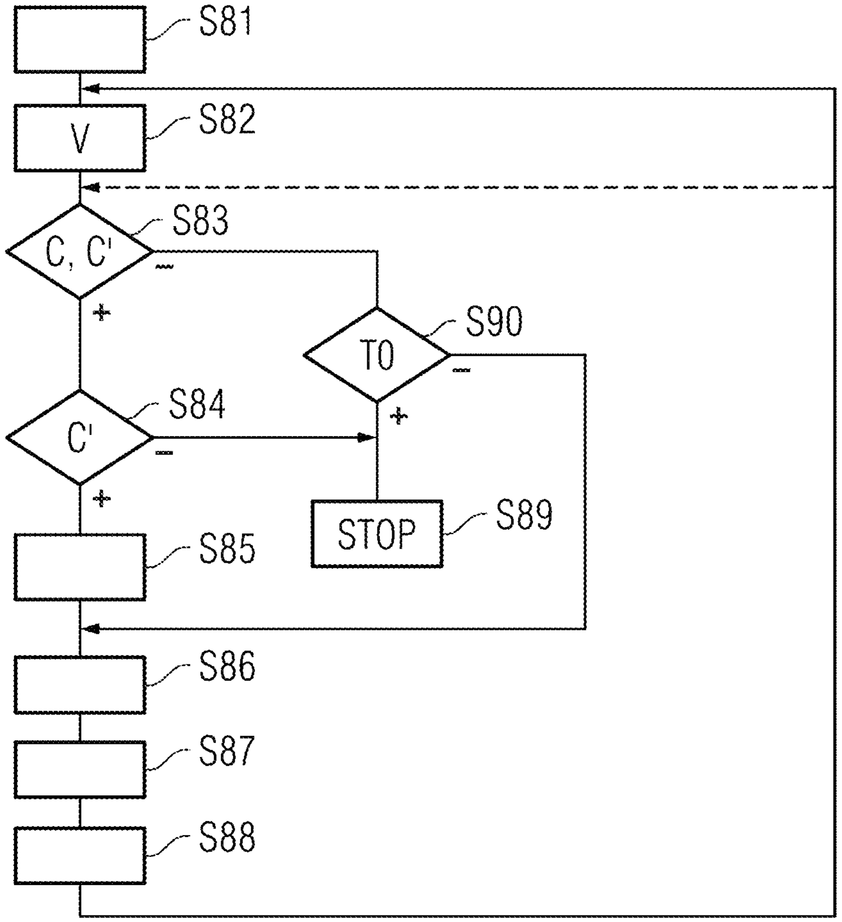

According to FIG. 11, the control apparatus 4 starts the timer 12 in step S81. In the case of the embodiment in FIGS. 10 and 11, the time period TO corresponds to the time period T2 for which the timer 16 of the monitoring apparatus 10 runs. In step S82, the control apparatus 4 receives the movement commands V. In step S83, the control apparatus 4 checks whether a collision signal C, C' has been transmitted to it by the evaluation apparatus 7. Steps S82 and S83 correspond to steps S11 and S12 in FIG. 3.

If a collision signal C, C' was transmitted to the control apparatus 4 in step S83, the control apparatus 4 proceeds to step S84. In step S84, the control apparatus 4 checks whether the transmitted collision signal C, C' has (exactly or at least approximately) the duration t2. If this is the case, the transmitted collision signal C, C' is a special collision signal C'. Therefore, the control apparatus 4 proceeds to step S85 in which it resets the timer 12 so that the time period T2 starts to run again.

In step S86, the control apparatus 4 then receives the sensor signals from the sensor system 5. In step S87, the control apparatus 4 ascertains actuation commands for the drive 3. In step S88, the control apparatus 4 outputs the ascertained actuation commands to the drive 3. The control apparatus 4 then returns to step S82 or, as indicated by the dashed line in FIG. 11, to step S83. Whether the control apparatus 4 returns to step S82 or step S83 can depend on the type of movement commands V. Steps S86 to S88 correspond to steps S14 to S16 in FIG. 3.

If the transmitted collision signal C, C' does not have the duration t2, the transmitted collision signal C, C' is a normal collision signal C. Therefore, the control apparatus 4 proceeds to step S89. In step S89, the control apparatus 4 immediately ends the active actuation of the drive 3, at least in the current direction of travel, and thus the movement of the moving element 2 in this direction of travel. Step S89 corresponds to step S13 in FIG. 3.

If the control apparatus 4 does not detect a collision signal C, C' in step S83, the control apparatus 4 proceeds to step S90. In step S90, the control apparatus 4 checks whether the timer 12 has expired. If this is the case, there is a malfunction of the evaluation apparatus 7 because a special collision signal C' was expected but not transmitted. Therefore, the control apparatus 4 proceeds to step S89. On the other hand, if the timer 12 has not yet expired, the control apparatus 4 proceeds to step S86.

The procedure in FIGS. 10 and 11 can be implemented regardless of whether or not the evaluation apparatus 7 is embodied with first-fault safety. However, in both cases, the time periods T1, T2 must be determined suitably. In particular, in the event of an embodiment of the evaluation apparatus 7 without first-fault safety, the time periods T1, T2 must be shorter than the fault tolerance time (usually referred to as FTT). If the fault tolerance time is, for example 100 ms, the time periods T1, T2 can, for example, be 80 ms and 81 ms. The numerical values mentioned are of course purely by way of example.

In summary, the present invention relates to the following:

In a normal mode of a medical device 1, a control apparatus 4 moves a moving element 2 of the medical device 1 in a controlled manner via a drive 3 when corresponding movement commands V are issued. In the normal mode, an evaluation apparatus 7 monitors a first-fault-safety contact element 6 arranged on the medical device 1 for actuation and, in the event of actuation, transmits a normal collision signal C via lines 8, 9 to the control apparatus 4 and a monitoring apparatus 10. In the event of a normal collision signal C being transmitted to it, the control apparatus 4 immediately ends the movement of the moving element 2, at least in the current direction of travel, and, at the latest after the predetermined waiting time has elapsed without actuation of the drive 3 as such, the monitoring apparatus 10 prevents the drive 3 from acting on the moving element 2. Either the control apparatus 4 or the monitoring apparatus 10 transmits a check command B to the evaluation apparatus 7 on the occurrence of a checking condition. In this case, the evaluation apparatus 7 transmits a respective special collision signal C' to the control apparatus 4 and the monitoring apparatus 10 via the lines 8, 9. In the absence of a special collision signal C' expected on the basis of a check command B, the control apparatus 4 blocks movement of the moving element 2, at least in the current direction of travel, and, at the latest after the predetermined waiting time has elapsed without actuation of the drive 3 as such, the monitoring apparatus 10 prevents the drive 3 from acting on the moving element 2.

The present invention has many advantages. In particular, division into a control path (C-path) and a monitoring path (P-path), which is common and proven in medical devices, can be retained while first-fault-safety monitoring for collisions can still be implemented. This enables damage to property and personal injury to be avoided in a simple manner. In particular in the case of the embodiment according to FIGS. 10 and 11, the evaluation apparatus 7 does not have to have first-fault safety and can therefore be implemented in a compact and cost-effective manner. Furthermore, in this case, operational safety can be substantially achieved by programming the control apparatus 4 and the monitoring apparatus 10, so existing devices 1 can also be easily retrofitted.

Although the invention has been illustrated and described in detail by example embodiments, the invention is not restricted by the disclosed examples and other variations can be derived herefrom by the person skilled in the art without departing from the scope of protection of the invention.

Independent of the grammatical term usage, individuals with male, female or other gender identities are included within the term.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SOC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, or instructions, some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible language), markup (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable read-only memory devices, or a mask read-only programmable memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. An operating method for a medical device, the method comprising:

moving, by a control apparatus of the medical device and in a normal mode of the medical device, a moving element of the medical device in a controlled manner via a drive when corresponding movement commands are issued to the control apparatus;

monitoring, by an evaluation apparatus and in the normal mode, a first-fault-safety contact element on the medical device for actuation and, if actuation is detected, transmitting a respective normal collision signal via respective lines to the control apparatus and a monitoring apparatus of the medical device, the monitoring apparatus being different from the control apparatus; and in response to a normal collision signal being transmitted, ending, by the control apparatus, the movement of the moving element at least in a current direction of travel, and preventing, by the monitoring apparatus, the drive from acting on the moving element, wherein the control apparatus or the monitoring apparatus transmits a check command to the evaluation apparatus on an occurrence of a checking condition, in response to a check command being transmitted, the evaluation apparatus transmits a respective special collision signal to the control apparatus and the monitoring apparatus via the lines, and in the absence of a special collision signal expected based on the check command, the control apparatus blocks movement of the moving element at least in the current direction of travel and the monitoring apparatus prevents the drive from acting on the moving element.

2. The operating method of claim 1, wherein the evaluation apparatus is a first-fault-safety evaluation apparatus and the checking condition occurs during the medical device being in a special mode in which actuation of the drive is blocked by the control apparatus.

3. The operating method of claim 2, wherein the special mode occurs during a power supply of the medical device having been switched on shortly beforehand or during a command for transition to the special mode having been issued by a higher-level apparatus.

4. The operating method of claim 3, wherein a normal collision signal has a minimum duration and the special collision signal is shorter than the minimum duration.

5. The operating method of claim 2, wherein a normal collision signal has a minimum duration and the special collision signal is shorter than the minimum duration.

6. A medical device comprising:

a moving element;

a drive;

a control apparatus, wherein, in a normal mode of the medical device, the control apparatus moves the moving element in a controlled manner via the drive when corresponding movement commands are issued to the control apparatus;

an evaluation apparatus;

a monitoring apparatus different from the control apparatus; and a first-fault-safety contact element on the medical device, wherein the evaluation apparatus is connected to the control apparatus and the monitoring apparatus via respective lines, the control apparatus or the monitoring apparatus is connected to the evaluation apparatus, and the control apparatus, the evaluation apparatus and the monitoring apparatus interact with one another according to the operating method of claim 2.

7. The operating method of claim 1, wherein the checking condition occurs upon an expiration of a predetermined monitoring period, a normal collision signal has a minimum duration and a special collision signal having a duration that is shorter than the minimum duration.

8. A medical device comprising:

a moving element;

a drive;

a control apparatus, wherein, in a normal mode of the medical device, the control apparatus moves the moving element in a controlled manner via the drive when corresponding movement commands are issued to the control apparatus;

an evaluation apparatus;

a monitoring apparatus different from the control apparatus; and a first-fault-safety contact element on the medical device, wherein the evaluation apparatus is connected to the control apparatus and the monitoring apparatus via respective lines, the control apparatus or the monitoring apparatus is connected to the evaluation apparatus, and the control apparatus, the evaluation apparatus and the monitoring apparatus interact with one another according to the operating method of claim 7.

9. A medical device comprising:

a moving element;

a drive;

a control apparatus, wherein, in a normal mode of the medical device, the control apparatus moves the moving element in a controlled manner via the drive when corresponding movement commands are issued to the control apparatus;

an evaluation apparatus;

a monitoring apparatus different from the control apparatus; and a first-fault-safety contact element on the medical device, wherein the evaluation apparatus is connected to the control apparatus and the monitoring apparatus via respective lines, the control apparatus or the monitoring apparatus is connected to the evaluation apparatus, and the control apparatus, the evaluation apparatus and the monitoring apparatus interact with one another according to the operating method of claim 1.

10. The medical device of claim 9, wherein the first-fault-safety contact element is on the moving element.

* * * * *